(12) United States Patent
Nowlin et al.

(10) Patent No.: US 7,871,405 B2
(45) Date of Patent: Jan. 18, 2011

(54) DETACHABLE GRID

(75) Inventors: Brett Nowlin, Bridgewater, MA (US); Arthur R. Madenjian, Winchester, MA (US); Richard Tah, Framingham, MA (US); Weenna Bucay-Couto, Burlington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 789 days.

(21) Appl. No.: 11/858,576

(22) Filed: Sep. 20, 2007

(65) Prior Publication Data
US 2008/0077089 A1 Mar. 27, 2008

Related U.S. Application Data

(60) Provisional application No. 60/846,493, filed on Sep. 21, 2006.

(51) Int. Cl.
*A61B 18/18* (2006.01)
(52) U.S. Cl. ............... 606/20; 606/129; 606/130; 604/116; 33/511
(58) Field of Classification Search ........... 606/1–52, 606/129–130, 96–98; 604/116; 600/7; 83/821–829; 408/115 R, 115 B, 241 G; 33/511
See application file for complete search history.

(56) References Cited

U.S. PATENT DOCUMENTS

| | | | |
|---|---|---|---|
| 5,957,935 A | 9/1999 | Brown et al. | |
| 6,036,632 A | 3/2000 | Whitmore et al. | |
| 6,142,991 A * | 11/2000 | Schatzberger | 606/21 |
| 6,398,711 B1 * | 6/2002 | Green et al. | 600/7 |
| 6,544,176 B2 | 4/2003 | Mikus et al. | |
| 6,579,262 B1 * | 6/2003 | Mick et al. | 604/116 |
| 6,846,315 B2 * | 1/2005 | Barzell et al. | 606/130 |
| 6,863,654 B2 | 3/2005 | Zappala et al. | |
| 2002/0198514 A1 * | 12/2002 | Barzell et al. | 606/1 |

(Continued)

FOREIGN PATENT DOCUMENTS

EP 1 374 951 A1 1/2004

OTHER PUBLICATIONS

*Notification of Transmittal of the International Search Report and the Written Opinion of the International Searching Authority, or the Declaration* (Form PCT/ISA/220) dated Jan. 18, 2008 issued in corresponding international application No. PCT/US2007/079038; together with the International Search Report (Form PCT/ISA/210) and the Written Opinion of the International Searching Authority (Form PCT/ISA/237).

(Continued)

*Primary Examiner*—Thomas J Sweet
*Assistant Examiner*—Amanda Scott
(74) *Attorney, Agent, or Firm*—Brown Rudnick LLP

(57) ABSTRACT

Medical devices can be positioned within a patient by use of apparatus and methods according to the invention. The apparatus and methods permit insertion of the medical devices into various locations of the patient's body without requiring removal and reinsertion of already-inserted medical devices. The apparatus and methods are typically used to place medical devices into a male patient's urinary system to treat a disease or condition. The medical devices can be cryoablation probes that are inserted into the prostate gland to treat prostate cancer, for example.

19 Claims, 4 Drawing Sheets

U.S. PATENT DOCUMENTS

| | | | |
|---|---|---|---|
| 2002/0198518 A1* | 12/2002 | Mikus et al. | 606/21 |
| 2003/0036770 A1* | 2/2003 | Markman | 606/187 |
| 2004/0024391 A1 | 2/2004 | Cytron et al. | |
| 2004/0143150 A1* | 7/2004 | Barzell et al. | 600/7 |
| 2004/0220444 A1 | 11/2004 | Hogendijk | |
| 2005/0234476 A1* | 10/2005 | Whitmore et al. | 606/130 |
| 2006/0224149 A1* | 10/2006 | Hillely | 606/21 |
| 2007/0276358 A1* | 11/2007 | Barzell et al. | 606/1 |
| 2009/0014015 A1* | 1/2009 | Tutar et al. | 128/898 |
| 2010/0262067 A1* | 10/2010 | Chornenky et al. | 604/20 |

OTHER PUBLICATIONS

Notification Concerning Transmittal of International Preliminary Report on Patentability dated Mar. 24, 2009.

CIVCO Medical Instruments; Product Release; Product Description: Percutaneous Localizer; Ref. No. 810-007; 2005.

CIVCO Medical Instruments; Product Description: Sterile Grids; Ref. Nos. 610-905; 610-906; 610-915; 610-916; 2004; www.civco.com.

CIVCO Medical Instruments; Accessories Kit Reference Guide; Apr. 26, 2004.

CIVCO Medical Instruments; Product Description: Disposable Accessory Kits; Ref. Nos. 610-909; 610-910; 2004; www.civco.com.

CIVCO Medical Instruments; Product Description: Non-Sterile RTP Adapter; Ref. no. 6600-R; 2004; www.civco.com.

CIVCO Medical Instruments; Grid Reference Guide; Apr. 28, 2004.

CIVCO Medical Instruments; Grid Adapter Reference Guide.

CIVCO Medical Instruments; AccuCARE Reference Guide; Apr. 26, 2004.

* cited by examiner

DETACHABLE GRID

This application claims priority to U.S. Provisional Patent Application No. 60/846,493, filed Sep. 21, 2006, entitled "Detachable Grid," the entire content of which is hereby incorporated by reference.

TECHNICAL FIELD

The invention relates generally to accurate and flexible positioning of medical devices within a patient to help treat diseases and/or other conditions such as prostate cancer and/or other diseases or conditions of the urinary system, for example.

BACKGROUND INFORMATION

Prostate cancer is one of the most common forms of cancer in men, and some of its traditional treatments can result in serious complications for the patient. Cryoablation is an emerging alternative that involves the controlled freezing of the prostate gland to destroy cancerous cells. In performing the procedure, the prostate is generally imaged and its size determined using an ultrasonic probe guided into the patient's rectum.

An aiming grid software program is typically activated and images of the prostate are projected on a screen. Under continuous monitoring with ultrasonic imaging, cryoablation probes are placed at predetermined sites within the prostate via the perineum using a "Cryo Grid," which is a brachytherapy-like grid fixed to an ultrasound stepper. The placement of the cryoablation probes is such that cancerous sites are effectively ablated while sparing the non-diseased areas.

It is sometimes necessary to reposition the grid to ensure that the cryoablation probes reach their intended targets. Removing the grid is difficult because some cryoablation probes will already be in place and thus passing through the grid.

SUMMARY OF THE INVENTION

The invention generally relates, in one aspect, to a grid that can be removed and repositioned quickly and easily to allow placement of additional cryoablation probes, leaving the deployed cryoablation probes in place and undisturbed.

The present invention provides apparatus and methods for facilitating treatment of diseases (of, for example, the urinary system) such as prostate cancer. In comparison to systems and methods presently in use, apparatus and methods according to the invention provide a medical professional with much greater flexibility in the placement of medical devices, such as cryoprobes, in patients.

In one particular embodiment according to the invention, an apparatus has one or more comb-like structures ("guides") that are inserted into a frame ("base plate"). The guides are used to constrain the movement of a medical device being introduced into a patient's body. Typically, the guides are used in pairs. Either one pair or two pairs can be used. The guides are used and placed such that each is perpendicular to each other and to an axis of the base plate. This can be accomplished by inserting each guide into different (e.g., perpendicular) sides of the base plate. When four guides (i.e., two pairs) are used, the guides comprising the second pair are inserted into different (e.g., perpendicular) sides of the base plate as well. Each side of the base plate can accommodate the insertion of one or more of the guides. The guides can be removed from the base plate, and there is no requirement that every side of the base plate receive a guide.

The guides, which in some embodiments are substantially planar, can include a series of parallel spaced prongs. Consequently, the perpendicular arrangement of the guides creates passages parallel (i.e., coaxial) to the axis of the base plate where the spaces between the prongs intersect at right angles. Medical devices then can be passed through these passages to their intended targets in the patient. While in the passages, the movement of the medical devices is limited to the direction of the passages, that is, in a direction parallel (i.e., coaxial) to the axis of the base plate. Undesirable angular movement of the medical devices thus is minimized or eliminated by the apparatus.

An embodiment of the invention includes an apparatus for use in a medical procedure to aid the insertion of one or more devices into the body of a patient, comprising a base plate having a periphery defining (i) a central aperture characterized at least in part by a longitudinal axis, (ii) a first insertion aperture, and (iii) a second insertion aperture, the first insertion aperture located on a first edge of the periphery and the second insertion aperture located on a second edge of the periphery; a first guide adapted to be removably insertable into the first insertion aperture, the first guide including a plurality of spaced prongs oriented in a single direction; and a second guide adapted to be removably insertable into the second insertion aperture, the second guide including a plurality of spaced prongs oriented in a single direction, the prongs of the first guide when inserted into the first insertion aperture, the prongs of the second guide when inserted into the second insertion aperture, and the longitudinal axis being orthogonal to each other and the inserted prongs of the first and second guides intersecting to form a plurality of passages within at least a portion of the central aperture, each of the plurality of passages having a longitudinal axis, and each of the plurality of passages for receiving one of the one or more devices.

In some embodiments, the second edge is adjacent and substantially perpendicular to the first edge. In some embodiments, the first guide is substantially planar. In some embodiments, the single direction of the plurality of spaced prongs of the first guide is within the plane of the first guide. In some embodiments, the second guide is substantially planar. In some embodiments, the single direction of the plurality of spaced prongs of the second guide is within the plane of the second guide. In some embodiments, the longitudinal axes of the passages formed by the first and second guides are parallel with the longitudinal axis of the base plate.

In some embodiments, the periphery of the base plate defines (i) a third insertion aperture, and (ii) a fourth insertion aperture, the third insertion aperture located on a third edge of the periphery and the fourth insertion aperture located on a fourth edge of the periphery, the apparatus further comprising a third guide adapted to be removably insertable into the third insertion aperture, the third guide including a plurality of spaced prongs oriented in a single direction; and a fourth guide adapted to be removably insertable into the fourth insertion aperture, the fourth guide including a plurality of spaced prongs oriented in a single direction, the prongs of the third guide when inserted into the third insertion aperture, the prongs of the fourth guide when inserted into the fourth insertion aperture, and the longitudinal axis being orthogonal to each other and the inserted prongs of the third and fourth guides intersecting to form a plurality of passages within at least a portion of the central aperture, each of the plurality of passages having a longitudinal axis, and each of the plurality of passages for receiving one of the one or more devices. In some embodiments, the third edge is adjacent and substantially perpendicular to the fourth edge. In some embodiments, the first edge comprises the third edge. In some embodiments, the second edge comprises the fourth edge. In some embodiments, the third guide is substantially planar. In some embodiments, the single direction of the plurality of spaced prongs of the third guide is within the plane of the third guide. In some embodiments, the fourth guide is substantially planar. In some embodiments, the single direction of the plurality of spaced prongs of the fourth guide is within the plane of the fourth guide. In some embodiments, the longitudinal axes of the passages formed by the third and fourth guides are parallel with the longitudinal axis of the base plate. In some embodiments, the longitudinal axes of the passages formed by the third and fourth intersecting guides and the longitudinal axes of the passages formed by the first and second intersecting guides are coaxial.

An embodiment of the invention includes a method for placing prostatic probes into a patient, the method comprising the steps of (a) providing a grid comprising (1) a base plate having a periphery defining (i) a central aperture characterized at least in part by a longitudinal axis, (ii) a first insertion aperture, and (iii) a second insertion aperture, the first insertion aperture located on a first edge of the periphery and the second insertion aperture located on a second edge of the periphery; (2) a first guide adapted to be removably insertable into the first insertion aperture, the first guide including a plurality of spaced prongs oriented in a single direction; (3) a second guide adapted to be removably insertable into the second insertion aperture, the second guide including a plurality of spaced prongs oriented in a single direction, the prongs of the first guide when inserted into the first insertion aperture, the prongs of the second guide when inserted into the second insertion aperture, and the longitudinal axis being orthogonal to each other and the inserted prongs of the first and second guides intersecting to form a plurality of passages within at least a portion of the central aperture, each of the plurality of passages having a longitudinal axis, and each of the plurality of passages for receiving one of the one or more devices; (4) a third guide adapted to be removably insertable into the third insertion aperture, the third guide including a plurality of spaced prongs oriented in a single direction; and (5) a fourth guide adapted to be removably insertable into the fourth insertion aperture, the fourth guide including a plurality of spaced prongs oriented in a single direction, the prongs of the third guide when inserted into the third insertion aperture, the prongs of the fourth guide when inserted into the fourth insertion aperture, and the longitudinal axis being orthogonal to each other and the inserted prongs of the third and fourth guides intersecting to form a plurality of passages within at least a portion of the central aperture, each of the plurality of passages having a longitudinal axis, wherein the longitudinal axes of the passages formed by the third and fourth intersecting guides and the longitudinal axes of the passages formed by the first and second intersecting guides are coaxial; (b) inserting at least one of the first guide, second guide, third guide, or fourth guide into at least one of the first insertion aperture, second insertion aperture, third insertion aperture, or fourth insertion aperture, respectively; (c) placing the base plate in a first position proximate the perineum of the patient; (d) inserting at least one cryoablation probe in the space between the prongs of at least one of the first guide, second guide, third guide, or fourth guide and into the patient's prostate; and (e) removing at least one of the first guide, second guide, third guide, or fourth guide while leaving the at least one cryoablation probe in place.

In other embodiments, the method described above further comprises the steps of (f) placing the base plate in a second position proximate the perineum of the patient; (g) inserting the at least one of the first guide, second guide, third guide, or fourth guide into at least one of the first insertion aperture, second insertion aperture, third insertion aperture, or fourth insertion aperture, respectively; and (h) inserting at least one cryoablation probe in the space between the prongs of at least one of the first guide, second guide, third guide, or fourth guide and into the patient's prostate.

This apparatus and/or variations of it can be used in cryoablation of the prostate, where the medical devices introduced into the passages of the apparatus and into the patient are cryoablation probes. After one or more of the cryoablation probes are introduced into the patient, the guides can be removed from the base plate, thereby allowing the medical professional to reposition the base plate without disrupting the position or placement of the cryoablation probes already in place. This is useful, for example, when the initial position of the base plate does not span the entire field where treatment is to be performed (e.g., where probes are to be inserted). In such an instance, the base plate is placed in a new position, and the guides are reinserted without disrupting the cryoablation probes already in place. The medical professional then inserts additional medical devices (e.g., cryoablation probes) using the guides located at the new position. This can be less traumatic for the patient, because it limits the number of times that the cryoablation probes need to be removed from and reinserted into the patient.

BRIEF DESCRIPTION OF THE DRAWINGS

The foregoing and other aspects, objects, features, and advantages of the invention, as well as the invention itself, will be more fully understood from the following description of various embodiments, when read together with the accompanying drawings, illustrating the principles of the invention by way of example only, in which.

DESCRIPTION

Figure 1:
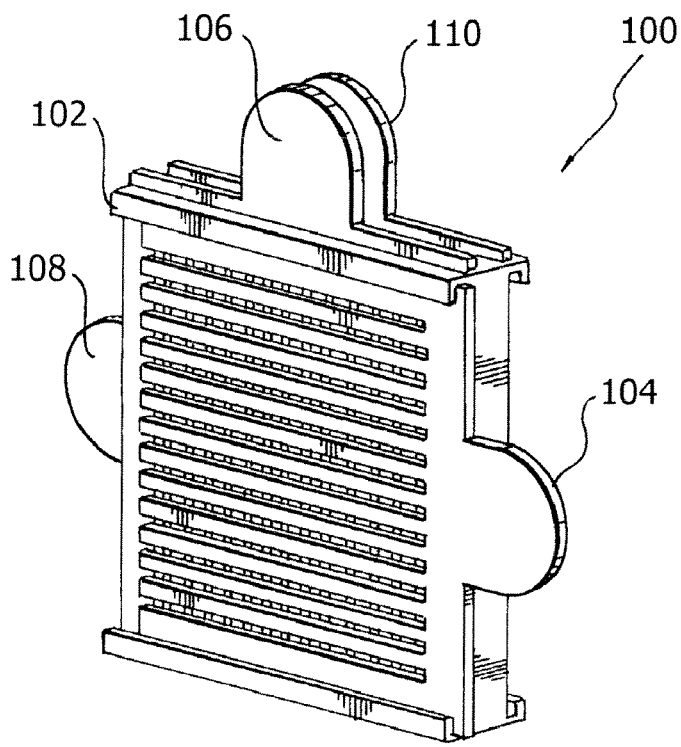
FIG. 1 is a schematic view depicting an apparatus for use in a medical procedure to aid the insertion of one or more devices into the body of a patient in accordance with an embodiment of the invention.

As shown in the drawings for the purposes of illustration, the invention can be embodied in apparatus and methods for facilitating treatment of diseases and/or other conditions such as prostate cancer, benign prostatic hyperplasia (BPH), and/or other diseases or conditions of the urinary system, for example. Embodiments of the invention are useful for providing a medical professional with flexibility in the placement of medical devices, such as cryoprobes, in patients. The patients can be humans or other mammals, and will be male patients when prostate cancer or BPH is being treated.

In brief overview, FIG. 1 is a schematic view depicting an apparatus 100 for use in a medical procedure to aid the insertion of one or more devices into the body of a patient in accordance with an embodiment of the invention. Specifically, the illustrative medical procedure involves cryoablation of the prostate gland, where cancerous sites in the prostate are ablated using controlled freezing. The controlled freezing is delivered to the prostate gland using one or more probes (e.g., "cryoprobes") inserted into the prostate gland at specific locations. The apparatus can be used in other medical procedures and is not limited to use only in the illustrative prostate cryoablation procedure.

Figure 2:
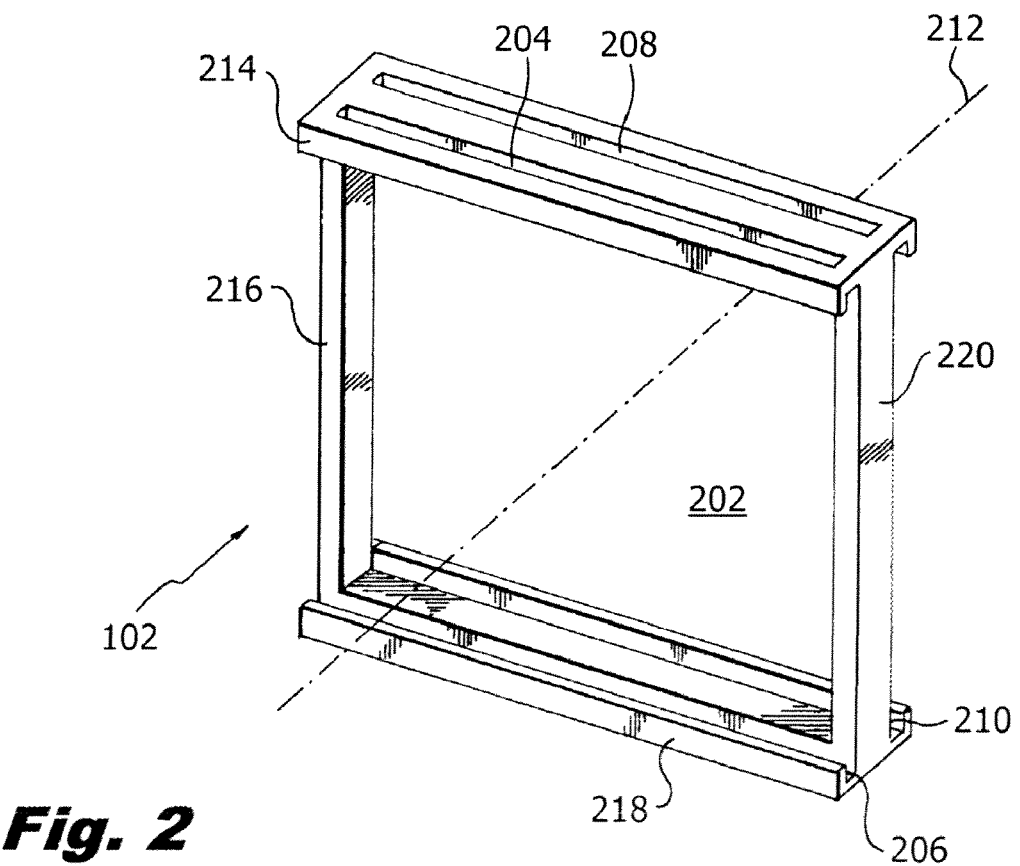
FIG. 2 is a schematic view depicting a base plate in accordance with an embodiment of the invention.

In one illustrative embodiment according to the invention, the apparatus 100 includes a base plate 102 that houses a first guide 104 and a second guide 106. As depicted in FIG. 2, the base plate 102 includes a first insertion aperture 204 that is located on a first edge 214. Similarly, the base plate 102 includes a second insertion aperture 206 that is located on a second edge 216. The first edge 214 and the second edge 216 are typically located on the periphery of the base plate 102. In some embodiments, the first edge 214 and the second edge 216 are adjacent and substantially perpendicular to each other.

The insertion apertures 204, 206 receive the guides 104, 106, thereby engaging the latter with the base plate 102. The insertion apertures 204, 206 allow the guides 104, 106 to be removed from the base plate 102 as well. In some embodiments, the insertion apertures 204, 206 include tracks wherein the guides 104, 106 slide into and out of the base plate 102.

Figure 3:
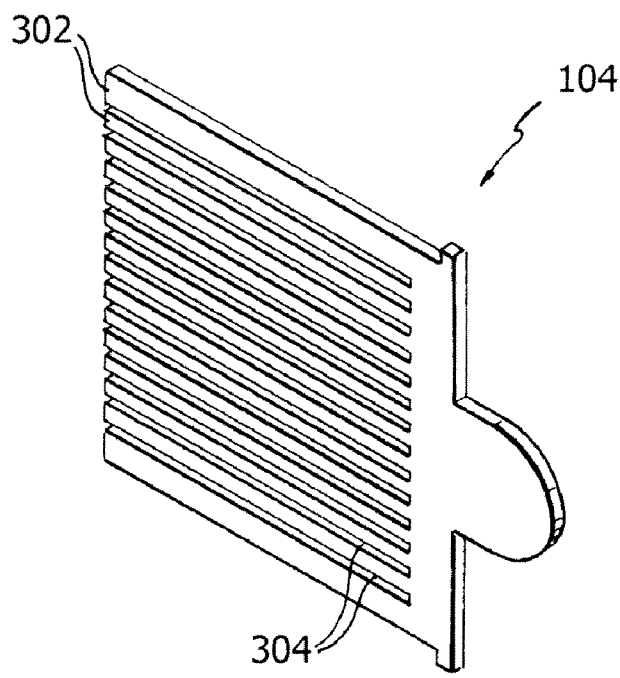
FIG. 3 is a schematic view depicting a guide in accordance with an embodiment of the invention.

As depicted in FIG. 3, the first guide 104 typically includes spaced prongs 302. Each prong 302 is separated from its neighboring prong by a space 304, each space having a width and a length. The space 304 between each prong 302 can be uniform (i.e., all spaces 304 having the same width and length), or it can vary (e.g., at least some of the spaces 304 having different widths, or lengths, or both). In either case, the prongs 302 are generally oriented in single direction. This single direction can be within the plane of the first guide 104. The first guide 104 can be, but need not be, substantially planar. Each of the aforementioned characteristics of the first guide 104 can apply to the second guide 106 as well.

Figure 4:
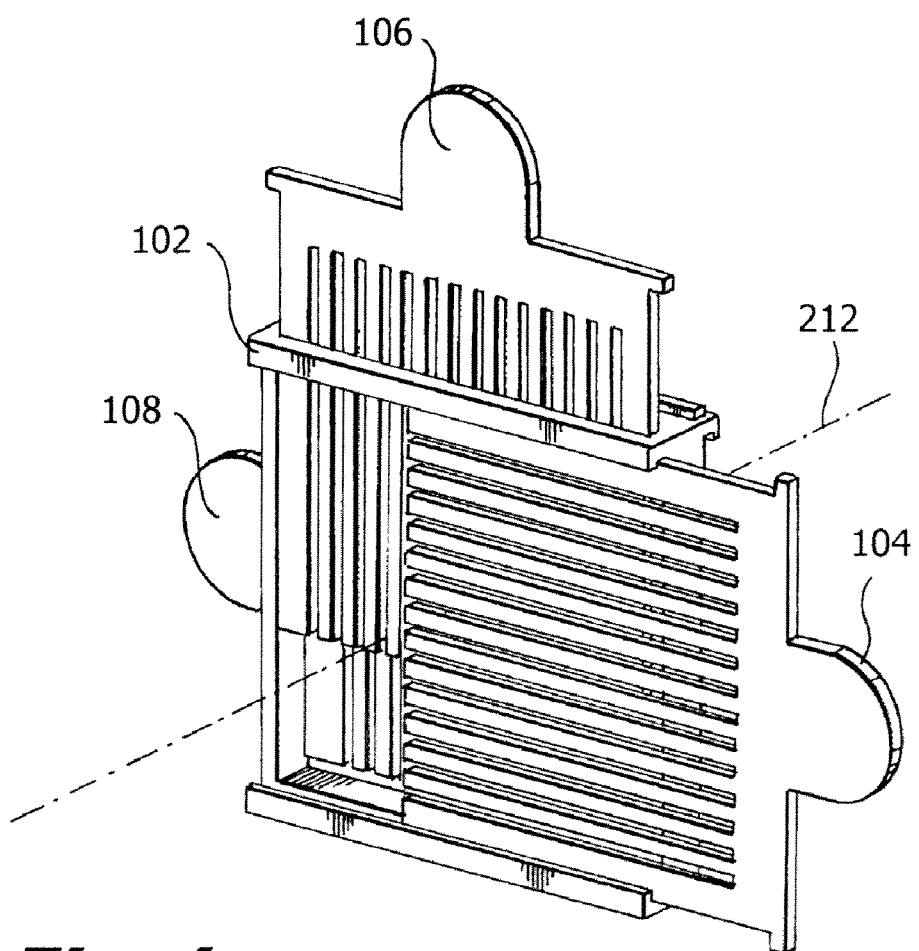
FIG. 4 is a schematic view depicting guides being inserted into the base plate of the apparatus in accordance with an embodiment of the invention.
Figure 5A:
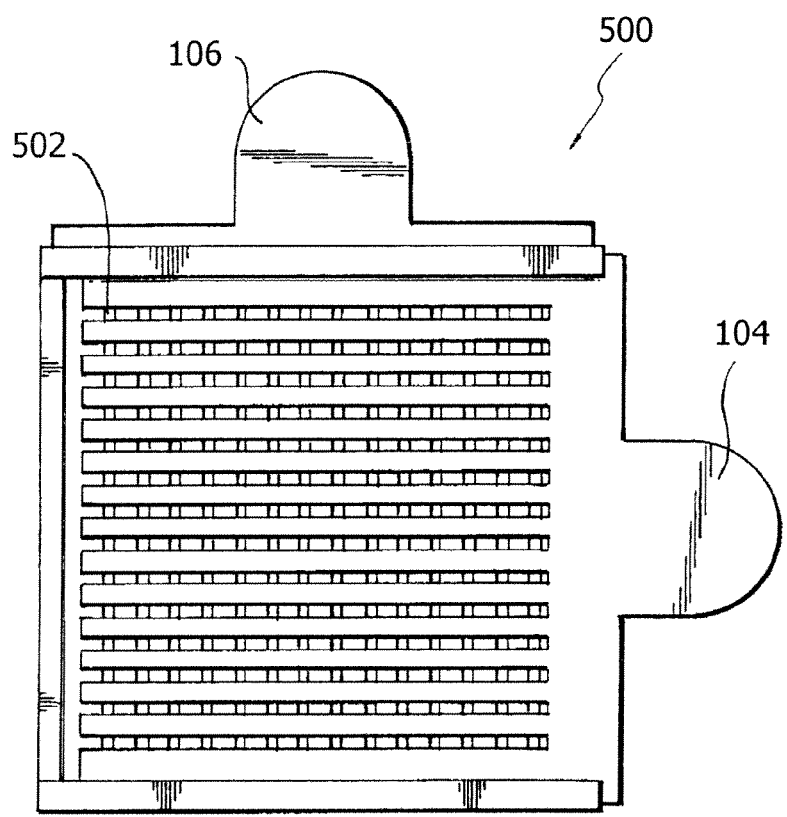
FIGS. 5A and 5B are schematic views depicting passages in the apparatus in accordance with an embodiment of the invention.
Figure 5B:
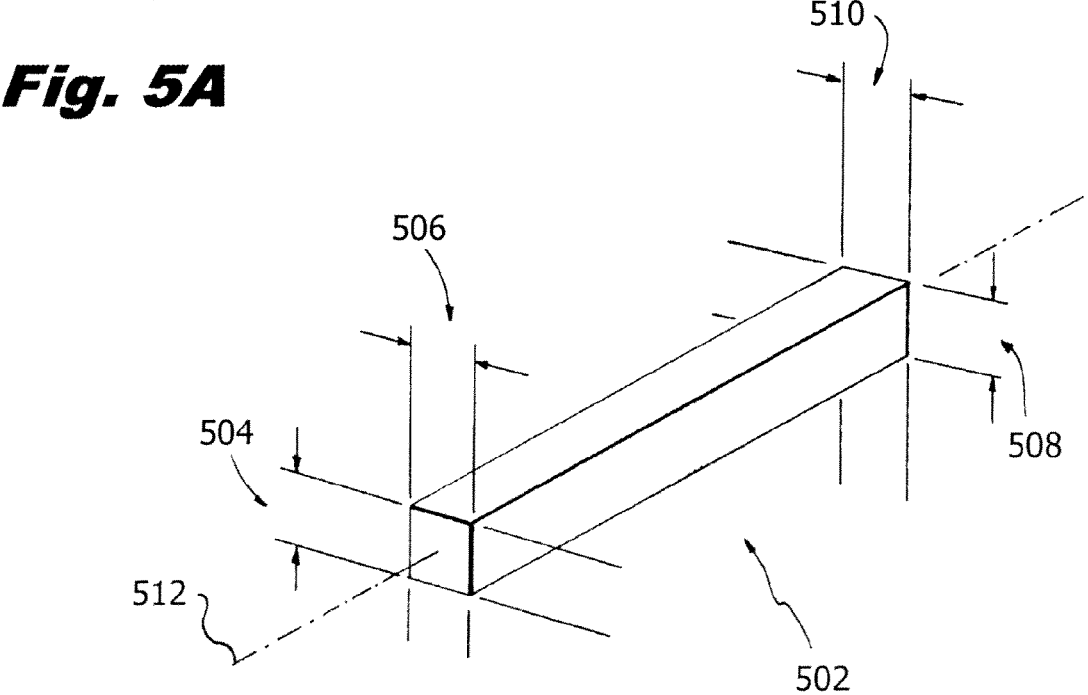

The base plate 102 includes a central aperture 202 that is perpendicular to a longitudinal axis 212 of the base plate 102. When the guides 104, 106 are inserted into the base plate 102, the locations of the insertion apertures 204, 206 position the guides 104, 106 perpendicular to each other and the longitudinal axis 212. FIG. 4 depicts this arrangement. Also, this configuration causes the spaced prongs 302 of the first guide 104 to be perpendicular to the spaced prongs 302 of the second guide 106, and the spaced prongs 302 of the guides 104, 106 to be perpendicular to the longitudinal axis 212 as well. In other words, the spaced prongs 302 of the guides 104, 106 (when the guides 104, 106 are inserted into the insertion apertures 204, 206) and the longitudinal axis 212 are orthogonal to each other. Consequently, the spaces 304 between the prongs 302 of the guides 104, 106 are perpendicular to each other and the longitudinal axis 212 as well, and form a series of passages 502 as shown in FIG. 5A. FIG. 5B, which is a detailed representative view of one of the passages 502, shows that each passage 502 is bounded in part by (i) a space 504 between the prongs 302 of the first guide 104, and (ii) a space 506 between the prongs 302 of the second guide 106. Each passage 502 forms a pathway through the guides 104, 106 along a longitudinal axis 512. The longitudinal axis 512 can be parallel to the longitudinal axis 212. These passages 502 receive medical devices, such as cryoprobes, allowing the medical devices to travel through the pathways, along the longitudinal axis 512, to their intended targets. Restricting the travel of the medical devices such that they move in the direction of the longitudinal axis 512 generally limits unintentional (and typically undesirable) angular movement of the medical devices.

In some embodiments, the apparatus 100 includes a third guide 108 and a fourth guide 110, as depicted in FIG. 1. The base plate 102 receives the third guide 108 via a third insertion aperture 208, and receives the fourth guide 110 via a fourth insertion aperture 210, thereby engaging the guides 108, 110 with the base plate 102. The insertion apertures 208, 210 allow the guides 108, 110 to be removed from the base plate 102 as well. The third insertion aperture 208 can be located on a third edge 218, and the fourth insertion aperture 210 can be located on a fourth edge 220. In some embodiments, the insertion apertures 208, 210 include tracks wherein the guides 108, 110 slide into and out of the base plate 102.

The third edge 218 and the fourth edge 220 are typically located on the periphery of the base plate 102. In certain embodiments, the third edge 218 and the fourth edge 220 are adjacent and substantially perpendicular to each other. In some embodiments, the first edge 214 includes the third edge 218. In further embodiments, the second edge 216 includes the fourth edge 220. In other words, the first guide 104 and the third guide 108 can be inserted into apertures located on the same edge (e.g., the first edge 214) of the base plate 102. Similarly, the second guide 106 and the fourth guide 110 can be inserted into apertures located on the same edge (e.g., the second edge 216) of the base plate 102.

The third guide 108 and the fourth guide 110 are configured similarly to the first guide 104. Consequently, each of the aforementioned characteristics (e.g., prongs 302, spaces 304, direction of the spaced prongs 302, and planarity or lack thereof) of the first guide 104 can apply to the third guide 108 and the fourth guide 110 as well. In some embodiments, however, one side of the apparatus 100 (e.g., the first guide 104 and the second guide 106, or the third guide 108 and the fourth guide 110) may be stationary (i.e., not removable).

When the guides 108, 110 are inserted into the base plate 102, the locations of the insertion apertures 208, 210 position the guides 108, 110 such that they are perpendicular to each other and the longitudinal axis 212 (i.e., all are orthogonal to each other). Consequently, the spaces 304 between the prongs 302 of the guides 108, 110 and the longitudinal axis 212 are orthogonal to each other, and form a series of passages like those described above in connection with FIG. 5A. These passages have longitudinal axes that, in some embodiments, are parallel to the longitudinal axis 112 of the base plate and, in other embodiments, are coaxial with the longitudinal axes 512.

In some embodiments, the third guide 108 and the fourth guide 110 are spaced apart from the first guide 104 and the second guide 106, typically because the third insertion aperture 208 and the fourth insertion aperture 210 are spaced apart from the first insertion aperture 204 and the second insertion aperture 206. One result of this spacing is the elongation of the passages 502, such that the passages 502 form pathways through all four guides 104, 106, 108, 110. In other words, in some embodiments, the extent of the passages 502 is from the area of the intersection of the first guide 104 and the second guide 106 to the area of the intersection of the third guide 108 and the fourth guide 110. This is depicted in FIG. 5B, where spaces 504, 506 bound the passage 502 at one end, and spaces 508, 510 bound the passage at the other end. (The spaces 508, 510 are the spaces between the prongs 302 of the third guide 108 and the fourth guide 110, respectively.) Elongating the passages 502 generally limits further the unintentional angular movement of the medical devices, because the longer pathways restrict their travel along a greater extent of the longitudinal axis 512.

Figure 6:
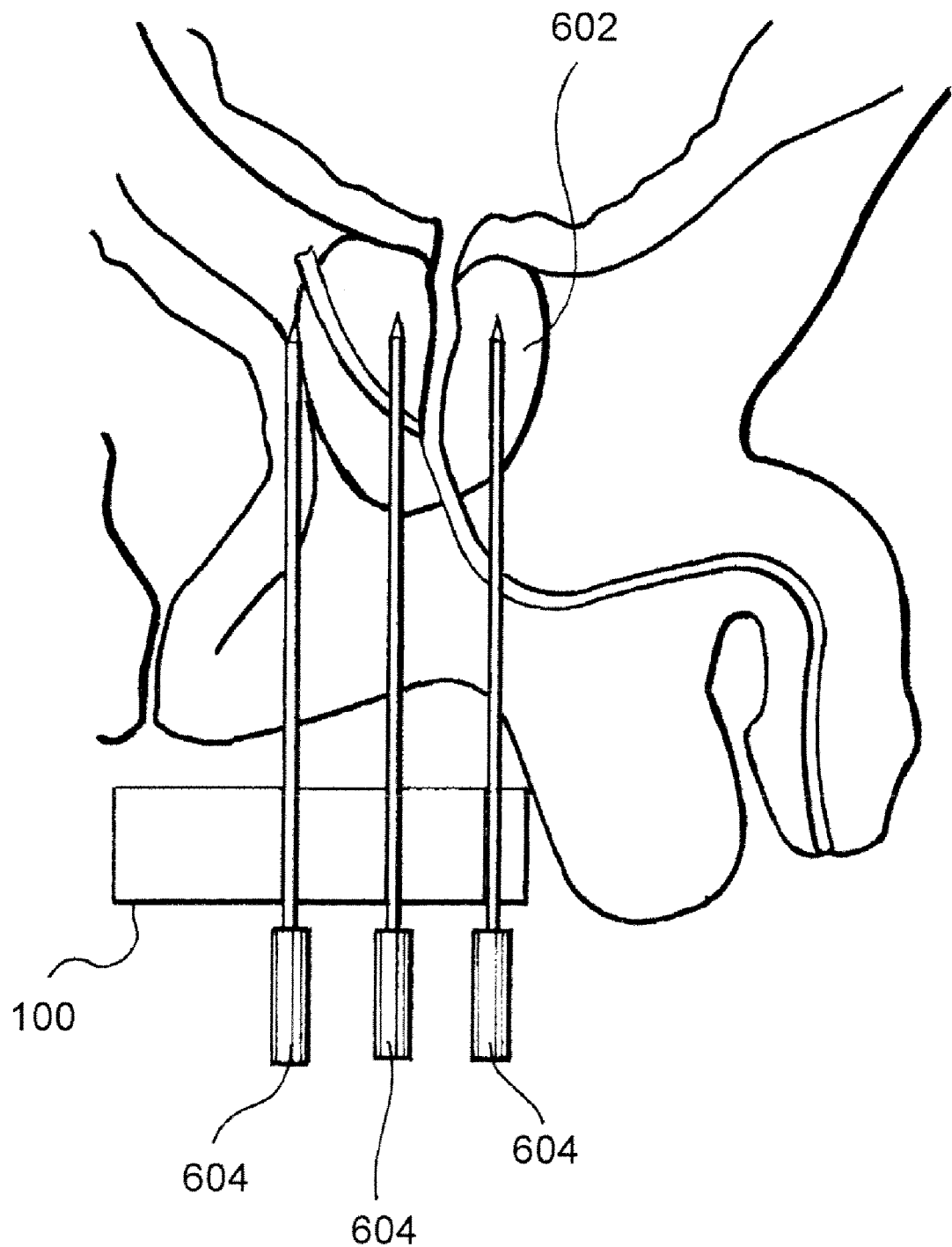
FIG. 6 is a schematic view depicting a use of the apparatus in accordance with an embodiment of the invention.

In brief overview, FIG. 6 is a schematic view of the male urinary system 600 showing the use of the apparatus 100 to aid the insertion of one or more devices into the body of a patient in a medical procedure in accordance with an embodiment of the invention. Specifically, the medical procedure involves cryoablation of the prostate gland 602, where cancerous sites in the prostate 602 are ablated using controlled freezing delivered by one or more cryoprobes 604. In this use, the apparatus 100 is termed a cryoablation grid.

During use, one or more of the first guide 104, the second guide 106, the third guide 108, or the fourth guide 110 are inserted into the base plate 102 such that the spaced prongs 302 of at least two of the guides are perpendicular to each other and the longitudinal axis of the 212 of the base plate 102. In some embodiments, all four guides 104, 106, 108, 110 are inserted into the base plate 102 such that (i) the spaced prongs 302 of the guides 104, 106 are perpendicular to each other, (ii) the spaced prongs 302 of the guides 108, 110 are perpendicular to each other, and (iii) the spaced prongs 302 of all cryoprobes 604 are perpendicular to the longitudinal axis of the 212 of the base plate 102. This configuration defines a series of passages 502 through the center aperture 202 that are arranged in grid configuration. The prongs 302 of the guides 104, 106, 108, 110 bound the sides of the passages 502, and the spaces 304 form the pathways through which the cryoprobes 604 travel. These pathways limit the (generally undesirable) angular movement of the cryoprobes 604.

Next, the apparatus 100 is placed in an initial position near the perineum of the patient and one or more cryoprobes 604 are inserted into one or more of the passages 502 and into the patient's prostate 602. The grid formed by the guides 104, 106, 108, 110 provides the medical professional with a reference to the precise location of each of the inserted cryoprobes 604. This is generally important, because the cryoablation typically is performed at specific locations in or on the prostate 602.

The guides 104, 106, 108, 110 are then removed from the base plate 102 while leaving the cryoprobes 604 in place. The base plate 102 is then moved to a second position, and some or all of the guides 104, 106, 108, 110 are reinserted into the base plate 102 without disturbing the cryoprobes 604 already in place. One or more additional cryoprobes 604 are then inserted into one or more of the passages 502 and into the patient, typically at locations that were inaccessible when the base plate 102 was in the initial position.

This configuration, where the guides 104, 106, 108, 110 can be removed, is advantageous because it gives the medical professional the flexibility to reposition the apparatus 100 as needed without removing the already-inserted cryoprobes 604. Consequently, the cryoprobes 604 can be inserted into the patient incrementally, with the apparatus 100 repositioned as many times as necessary during the insertion procedure, to treat the entire affected area. This eliminates the constraint that the apparatus 100 be maintained in a single position to avoid disrupting the cryoprobes 604.

In some embodiments, less than all four of the guides 104, 106, 108, 110 are inserted into the base plate 102. For example, using only one guide, such as the first guide 104, allows for insertion of the cryoprobes 604 along an axis (e.g., parallel to the spaces 304) or angularly. Placement of the cryoprobes 604 by free hand is possible if none of the guides 104, 106, 108, 110 are inserted into the base plate 102.

From the foregoing, it will be appreciated that apparatus and methods according to the invention afford a simple and effective way to facilitate treatment of diseases and/or conditions of a human or other mammal patient such as diseases and/or conditions of the patient's urinary system including, for example, prostate cancer or BPH. The apparatus and methods provide a medical professional with flexibility in the placement of medical devices, such as cryoprobes, in patients. Also, the apparatus and methods described above can be used in other applications such as, for example, guiding biopsy, guiding radio frequency ("RF") probes, guiding local drug delivery (such as chemotherapy in pellet forms, gel form, etc.) with a needle or obturator, brachyseed therapy, as well as with other ablation devices such as ferromagnetic thermal ablators and in photodynamic therapy.

The invention can be embodied in other specific forms without departing from the spirit or essential characteristics thereof. The foregoing embodiments are to be considered in all respects illustrative rather than limiting of the invention. The invention is not limited only to what is shown or described.

What is claimed is:

1. A method for placing prostatic cryoablation probes into a patient, the method comprising the steps of:
   (a) providing a cryoablation grid comprising:
      (1) a base plate having a periphery defining (i) a central aperture characterized at least in part by a longitudinal axis, (ii) a first insertion aperture, and (iii) a second insertion aperture, the first insertion aperture located on a first edge of the periphery and the second insertion aperture located on a second edge of the periphery;
      (2) a first guide adapted to be removably insertable into the first insertion aperture, the first guide including a plurality of spaced prongs oriented in a single direction;
      (3) a second guide adapted to be removably insertable into the second insertion aperture, the second guide including a plurality of spaced prongs oriented in a single direction, the prongs of the first guide when inserted into the first insertion aperture, the prongs of the second guide when inserted into the second insertion aperture, and the longitudinal axis being orthogonal to each other and the inserted prongs of the first and second guides intersecting to form a plurality of passages within at least a portion of the central aperture, each of the plurality of passages having a longitudinal axis, and each of the plurality of passages for receiving one of the one or more devices;
      (4) a third guide adapted to be removably insertable into the third insertion aperture, the third guide including a plurality of spaced prongs oriented in a single direction; and
      (5) a fourth guide adapted to be removably insertable into the fourth insertion aperture, the fourth guide including a plurality of spaced prongs oriented in a single direction, the prongs of the third guide when inserted into the third insertion aperture, the prongs of the fourth guide when inserted into the fourth insertion aperture, and the longitudinal axis being orthogonal to each other and the inserted prongs of the third and fourth guides intersecting to form a plurality of passages within at least a portion of the central aperture, each of the plurality of passages having a longitudinal axis, wherein the longitudinal axes of the passages formed by the third and fourth intersecting guides and the longitudinal axes of the passages formed by the first and second intersecting guides are coaxial;

(b) inserting at least one of the first guide, second guide, third guide, or fourth guide into at least one of the first insertion aperture, second insertion aperture, third insertion aperture, or fourth insertion aperture, respectively;

(c) placing the base plate in a first position proximate the perineum of the patient;

(d) inserting at least one cryoablation probe in the space between the prongs of at least one of the first guide, second guide, third guide, or fourth guide and into the patient's prostate; and (e) removing at least one of the first guide, second guide, third guide, or fourth guide while leaving the at least one cryoablation probe in place.

2. The method of claim 1 further comprising the steps of:

(f) placing the base plate in a second position proximate the perineum of the patient;

(g) inserting the at least one of the first guide, second guide, third guide, or fourth guide into at least one of the first insertion aperture, second insertion aperture, third insertion aperture, or fourth insertion aperture, respectively; and (h) inserting at least one cryoablation probe in the space between the prongs of at least one of the first guide, second guide, third guide, or fourth guide and into the patient's prostate.

3. An apparatus for use in a medical procedure to aid the insertion of one or more devices into the body of a patient, comprising:

a base plate having a periphery defining (i) a central aperture characterized at least in part by a longitudinal axis, (ii) a first insertion aperture, and (iii) a second insertion aperture, the first insertion aperture located on a first edge of the periphery and the second insertion aperture located on a second edge of the periphery;

a first guide adapted to be removably insertable into the first insertion aperture, the first guide including a plurality of spaced prongs oriented in a single direction; and a second guide adapted to be removably insertable into the second insertion aperture, the second guide including a plurality of spaced prongs oriented in a single direction, the prongs of the first guide when inserted into the first insertion aperture, the prongs of the second guide when inserted into the second insertion aperture, and the longitudinal is being orthogonal to each other and the inserted prongs of the first and second guides intersecting to form a plurality of passages within at least a portion of the central aperture, each of the plurality of passages having a longitudinal axis, and each of the plurality of passages for receiving one of the one or more devices.

4. The apparatus of claim 3, wherein the second edge is adjacent and substantially perpendicular to the first edge.

5. The apparatus of claim 3, wherein the first guide is substantially planar.

6. The apparatus of claim 3, wherein the single direction of the plurality of spaced prongs of the first guide is within the plane of the first guide.

7. The apparatus of claim 3, wherein the second guide is substantially planar.

8. The apparatus of claim 3, wherein the single direction of the plurality of spaced prongs of the second guide is within the plane of the second guide.

9. The apparatus of claim 3, wherein the longitudinal axes of the passages formed by the first and second guides are parallel with the longitudinal axis of the base plate.

10. The apparatus of claim 3, wherein the periphery of the base plate defines (i) a third insertion aperture, and (ii) a fourth insertion aperture, the third insertion aperture located on a third edge of the periphery and the fourth insertion aperture located on a fourth edge of the periphery, the apparatus further comprising:

a third guide adapted to be removably insertable into the third insertion aperture, the third guide including a plurality of spaced prongs oriented in a single direction; and a fourth guide adapted to be removably insertable into the fourth insertion aperture, the fourth guide including a plurality of spaced prongs oriented in a single direction, the prongs of the third guide when inserted into the third insertion aperture, the prongs of the fourth guide when inserted into the fourth insertion aperture, and the longitudinal axis being orthogonal to each other and the inserted prongs of the third and fourth guides intersecting to form a plurality of passages within at least a portion of the central aperture, each of the plurality of passages having a longitudinal axis, and each of the plurality of passages for receiving one of the one or more devices.

11. The apparatus of claim 10, wherein the third edge is adjacent and substantially perpendicular to the fourth edge.

12. The apparatus of claim 10, wherein the first edge comprises the third edge.

13. The apparatus of claim 10, wherein the second edge comprises the fourth edge.

14. The apparatus of claim 10, wherein the third guide is substantially planar.

15. The apparatus of claim 10, wherein the single direction of the plurality of spaced prongs of the third guide is within the plane of the third guide.

16. The apparatus of claim 10, wherein the fourth guide is substantially planar.

17. The apparatus of claim 10, wherein the single direction of the plurality of spaced prongs of the fourth guide is within the plane of the fourth guide.

18. The apparatus of claim 10, wherein the longitudinal axes of the passages formed by the third and fourth guides are parallel with the longitudinal axis of the base plate.

19. The apparatus of claim 10, wherein the longitudinal axes of the passages formed by the third and fourth intersecting guides and the longitudinal axes of the passages formed by the first and second intersecting guides are coaxial.

* * * * *